United States Patent [19]

Dyke

[11] Patent Number: 4,874,090
[45] Date of Patent: Oct. 17, 1989

[54] SELF-SEAL STERILIZATION POUCH

[75] Inventor: Denis G. Dyke, Edinboro, Pa.

[73] Assignee: American Sterilizer Company, Erie, Pa.

[21] Appl. No.: 261,197

[22] Filed: Oct. 24, 1988

[51] Int. Cl.$^4$ .............................................. B65D 33/16
[52] U.S. Cl. .................................. 206/439; 206/484.1; 206/632
[58] Field of Search ............... 206/363, 438, 439, 484, 206/484.1, 632, 633

[56] References Cited

U.S. PATENT DOCUMENTS

| | | | |
|---|---|---|---|
| 2,400,406 | 5/1946 | Godoy | 229/79 |
| 3,702,171 | 11/1972 | Levine | 229/79 |
| 4,194,622 | 3/1980 | Lewis | 206/363 |
| 4,276,982 | 7/1981 | Sibrava et al. | 383/84 |
| 4,358,015 | 11/1982 | Hirsch | 206/439 |
| 4,402,453 | 9/1983 | Regenstein, Jr. | 206/439 |
| 4,470,153 | 9/1984 | Kenan | 206/439 |
| 4,660,721 | 4/1987 | Mykleby | 206/439 |
| 4,714,595 | 12/1987 | Anthony | 206/439 |

Primary Examiner—Jimmy G. Foster
Attorney, Agent, or Firm—Kirkpatrick & Lockhart

[57] ABSTRACT

A sterilizable pouch for holding items during sterilization and for storing such items in a sterile condition following sterilization. The pouch includes a first member and a second opposing member. The first member extends outwardly beyond one edge of the second member to define a flap. An opening is defined between the one edge of the second member and the flap. The remaining edges of the first and second members are sealed to one another to define the pouch. An adhesive backed strip having a removable liner over the adhesive is connected along one edge to the second member adjacent to or spaced from the opening and is dimensioned to cover the opening and the flap when the liner is removed' and the adhesive backed strip is pressed against the opening and the flap.

8 Claims, 1 Drawing Sheet

SELF-SEAL STERILIZATION POUCH

BACKGROUND OF THE INVENTION

1. Field of the Invention

The present invention relates to sterilization pouches for holding items during sterilization, and more particularly, to a sterilizable pouch having an improved means of sealing the pouch opening.

2. Description of the Prior Art

Sterilizable pouches are well known in the art. Hospital type pouches consist generally of a paper sheet which is permeable to gases but impermeable to microorganisms and an opposing transparent plastic sheet which is impermeable to gases and microorganisms. The paper and plastic sheets are typically heat sealed along three or four edges.

Lewis, U.S. Pat. No. 4,194,622 illustrates a sterilizable pouch which is sealed on all four edges. A slit adjacent one edge and between two side edges provides access to the interior of the pouch. An adhesive strip on the paper sheet between the slit and the one edge of the paper sheet is provided so that when folded over, it covers and seals the slit.

Sibrava et al., U.S. Pat. No. 4,276,982 discloses a sterilizable pouch which is sealed on three edges. An opening is defined between the fourth edge of the plastic sheet and a flap created by an extension of the paper sheet. An adhesive strip on the paper flap spaced from the opening provides a seal for the opening when the flap is folded over so that the adhesive strip contacts the opening and the plastic sheet. Alternatively, the adhesive strip can be placed on the plastic sheet adjacent to but spaced from the unsealed fourth edge. The paper flap is folded over the unsealed edge and pressed against the adhesive strip to provide the seal for the opening in the pouch.

It has been observed that pouches having foldable flaps to cover the opening suffer from poor alignment of the flap when affixing to the paper and plastic ends. Wrinkles in the seal provide air channels for the entry of microorganisms.

A commercially available sterilization pouch is heat sealed on each of its four edges. An opening is provided by a slit in the plastic sheet similar to that shown in Lewis, U.S. Pat. No. 4,194,622. A seal for the opening is provided by an adhesive backed paper strip connected to the plastic sheet adjacent to and spaced from the slit. A removable liner covers the adhesive side of the paper strip. When it is necessary to close the slit to seal the pouch, the liner is removed and the paper member pressed against the slit.

The pouches having an opening provided by a slit have been observed to limit the ease with which items can be placed into the pouch and frequently tear when the pouches are loaded.

An object of the present invention is to provide a sterilizable pouch which has an improved means of sealing the opening to avoid the creation of air channels. A further object of the present invention is to provide such a pouch with easy access to the opening so that tearing is avoided.

SUMMARY OF THE INVENTION

The objects of the present invention are satisfied by a sterilizable pouch which includes a first sheet-like member and a second sheet-like member. The first and second members are both made of a material which is impermeable to microorganisms. One or both of the first and second members has at least a portion thereof made of a material which is permeable to gases. The first member extends outwardly beyond one edge of the second member to define a flap. The edge of the second member and the flap define an opening therebetween. The first and second members are sealed to one another along all edges thereof except for the opening to define the pouch for receiving items to be sterilized.

The pouch also includes sealing means having an upper surface and an adhesive coated lower surface connected along one edge to the second member proximate the opening. A liner for removably covering the adhesive coated lower surface is provided.

The sealing means is dimensioned to cover the opening and at least a portion of the flap adjacent the opening when the liner is removed and the adhesive backed lower surface is pressed against the opening and the flap to close and seal the opening. The pouch is preferably generally rectangular in shape and has access means for unsealing the pouch along the sealed edges.

BRIEF DESCRIPTION OF THE DRAWING

The present invention can be better understood by reference to the drawings in which.

DETAILED DESCRIPTION OF THE PREFERRED EMBODIMENT

Figure 1:
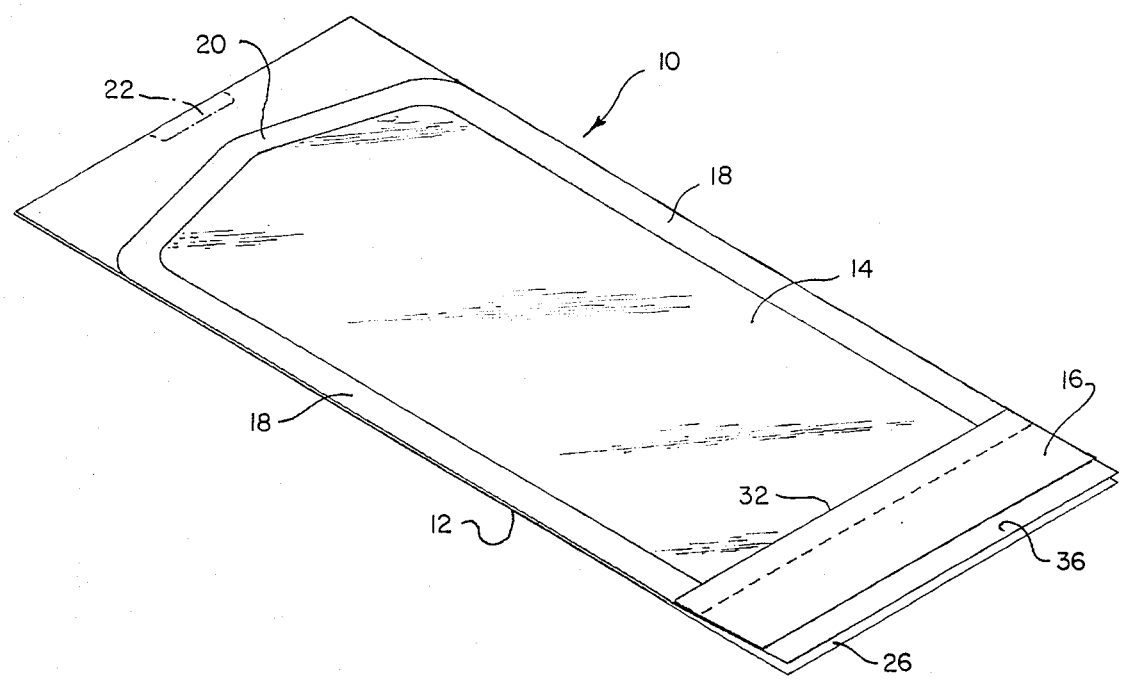
FIG. 1 illustrates the preferred embodiment of the self sealing sterilization pouch of the present invention.
Figure 2:
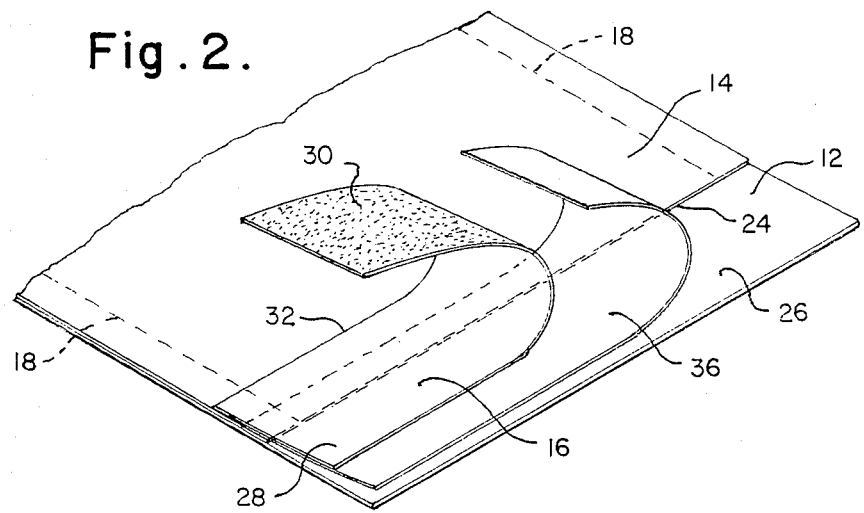
FIG. 2 illustrates an enlarged view of the sealing means and opening of the sterilization pouch of FIG. 1.

The preferred embodiment of the sterilizable pouch 10 of the present invention is illustrated in FIGS. 1 and 2. The pouch 10 includes generally a first sheet-like member 12, a second sheet-like member 14 and a sealing member 16. The first and second members, 12 and 14, are rectangular shaped, opposing, flat sheets sealed on three of four sides by a marginal heat seal 18 to define the pouch 10 between the opposing members. The chevron configuration 20 at the bottom of pouch 10 provides an access means to facilitate manual opening of the pouch 10 to remove the contents following sterilization by peeling the first and second members apart. While the chevron shape is preferred, the access means may be any suitable shape. It can be formed by having the seal at one portion of the pouch 10 spaced from an edge of at least one of the first or second members, 12 and 14. A cut away section 22 is provided in one of the members 12 or 14 to make it easier to grasp and separate the members, 12 and 14.

The first member 12 extends outwardly beyond second member 14 on the fourth side to define a flap 26. An opening 24 is defined on the unsealed fourth side between the first and second members, 12 and 14, and more specifically, between the unsealed fourth edge of the second member 14 and the flap 26 of first member 12.

Referring to FIG. 2, sealing member 16 is an adhesive backed strip having an upper surface 28 and a lower surface 30. One edge 32 of the sealing member 16 is connected to the second member 14 proximate the opening 24. The sealing member 16 may be connected at, adjacent to or spaced from the opening 24. Edge 32 of sealing member 16 is preferably parallel to opening 24 and extends along the full width of the second member 14. Edge 32 is preferably permanently connected to the second member 14, as shown in FIG. 1, to prevent the inadvertant removal and loss of the sealing member 16 and to enhance the alignment of sealing member 16 across the opening 24.

The lower surface 30 of sealing member 16 is coated in any suitable manner with a pressure sensitive adhesive. A readily removable release liner 36 covers the adhesive coating of lower surface 30 until the user is ready to seal opening 24 of pouch 10. When the release liner 36 is peeled away from the adhesive, the opening 24 can be closed by pressing sealing member 16 against the portion of second member 14 between edge 32 and opening 24, opening 24 and flap 26 of first member 12.

The first and second members 12 and 14, can both be made of a paper material which is impermeable to microorganisms but permeable to gases, such as steam and ethylene oxide. One commercially available source of the synthetic paper is made by duPont and sold under the trademark Tyvek. Natural papers may also be used.

The members 12 and 14 may also both be made of a thermally stable, preferably transparent, plastic material which is impermeable to microorganisms. The plastic material can be impermeable to gases, thus, in this embodiment of pouch 10, at least a portion of one or both of first and second members 12 and 14 would have to be made of a material which is permeable to gases. In the preferred embodiment, the first member 12 is made of a paper material and the second member 14 is made of the plastic laminate material.

The pouch 10 of the present invention provides both the ease of access of an open end 24 and a self aligning sealing member 16. Because sealing member 16 does not have to be folded over to seal the opening, the occasion for poor alignment resulting in wrinkles and air channels is avoided.

Pouch 10 is used in the same manner as known sterilization pouches. The items to be sterilized are placed in the pouch through opening 24. The opening is sealed as described above by pressing the adhesive backed sealing member 16 over the second member 14, opening 24 and flap 26. The pouch is then ready for exposure to a sterilization process. Any suitable known indicators to monitor effective sterilization can be incorporated into the pouch 10. The sterilized items can be stored in the pouch until ready for use. At that time, the first and second sheet-like members are peeled apart at the chevron shaped end of the pouch and the items removed.

I claim:

1. A sterilizable pouch comprising:
    a first sheet-like member made of a material which is impermeable to microorganisms and a second sheet-like member, opposing said first member, made of a material which is impermeable to microorganisms, and one or both of said first and second members having at least a portion thereof made of a material which is permeable to gases, said first member extending outwardly beyond one edge of said second member to define a flap, said edge of said second member and said flap defining an opening therebetween, said first member and said second member being sealed to one another along all edges thereof except for said opening to define said pouch for receiving items to be sterilized;
    sealing means having an upper surface and an adhesive coated lower surface connected along one edge to said second member proximate said opening; and
    a liner for removably covering said adhesive coated lower surface;
    said sealing means being dimensioned to cover said opening and at least a portion of said flap adjacent said opening when said liner is removed and said adhesive coated lower surface is pressed against said opening and said flap to close and seal said opening.

2. The pouch recited in claim 1 wherein said first member is made of a paper which is permeable to gases.

3. The pouch recited in claim 1 wherein said first member is made of a thermally stable plastic.

4. The pouch recited in claim 1 wherein said second member is made of a paper which is permeable to gases.

5. The pouch recited in claim 1 wherein said second member is made of a thermally stable plastic.

6. The pouch recited in claim 1 further comprising access means for unsealing said pouch along said sealed edges.

7. The pouch recited in claim 6 wherein the seal at one portion of said pouch, is spaced from an edge of at least one of said first and second members to define said access means.

8. The pouch recited in claim 7 wherein the seal at said portion of said pouch defining said access means is chevron-shaped.

* * * * *